(12) United States Patent
Starobin et al.

(10) Patent No.: US 9,144,682 B2
(45) Date of Patent: *Sep. 29, 2015

(54) METHOD AND SYSTEM OF STIMULATION OF NERVE TISSUE WITH A SEQUENCE OF SPATIALLY DISTRIBUTED RESONANT SUB-THRESHOLD ELECTRICAL STIMULI

(71) Applicant: The University of North Carolina Greensboro, Greensboro, NC (US)

(72) Inventors: Joseph M. Starobin, Greensboro, NC (US); Vivek Varadarajan, Greensboro, NC (US)

(73) Assignee: The University of North Carolina Greensboro, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/475,949

(22) Filed: Sep. 3, 2014

(65) Prior Publication Data

US 2015/0057723 A1    Feb. 26, 2015

Related U.S. Application Data

(63) Continuation of application No. 13/988,728, filed as application No. PCT/US2011/062807 on Dec. 1, 2011, now Pat. No. 8,855,787.

(60) Provisional application No. 61/424,758, filed on Dec. 20, 2010.

(51) Int. Cl.
*A61N 1/00* (2006.01)
*A61N 1/36* (2006.01)
*A61N 1/04* (2006.01)

(52) U.S. Cl.
CPC .......... *A61N 1/36171* (2013.01); *A61N 1/0456* (2013.01); *A61N 1/36103* (2013.01); *A61N 1/36139* (2013.01); *A61N 1/36164* (2013.01); *A61N 1/36178* (2013.01)

(58) Field of Classification Search
CPC ....... A61N 1/04; A61N 1/36; A61N 1/36103; A61N 1/0456; A61N 1/02
See application file for complete search history.

(56) References Cited

U.S. PATENT DOCUMENTS 5,643,330 A    7/1997    Holsheimer et al.
6,564,103 B2    5/2003    Fischer et al.

(Continued)

OTHER PUBLICATIONS

International Search Report and Written Opinion, PCT/US2011/062807, mailed Mar. 9, 2012.

*Primary Examiner* — Robert N Wieland
(74) *Attorney, Agent, or Firm* — Myers Bigel Sibley & Sajovec, P.A.

(57) ABSTRACT

The present invention provides a method of stimulating an excitable tissue (e.g., in vitro, in vivo) with a primary electrical stimulus through a primary electrode at a primary stimulation frequency, to produce a propagating action potential in the excitable tissue. The invention is carried out by concurrently stimulating the excitable tissue with a secondary electrical stimulus through at least one secondary electrode at a secondary stimulation frequency. The primary and secondary stimulation frequencies are preferably different from one another. The secondary electrical stimulus preferably has an amplitude not more than one third that of the primary electrical stimulus. Preferably, propagation of the action potential in the excitable tissue is enhanced (e.g., when propagation of action potentials in the tissue is otherwise unstable, partially blocked, or fully blocked). Apparatus for carrying out the method is also described.

22 Claims, 6 Drawing Sheets

(56) References Cited

U.S. PATENT DOCUMENTS

| | | |
|---|---|---|
| 7,035,691 B2 | 4/2006 | Campos |
| 7,689,289 B2 | 3/2010 | King |
| 2006/0149337 A1 | 7/2006 | John |
| 2008/0208285 A1 * | 8/2008 | Fowler et al. .............. 607/45 |
| 2008/0208287 A1 | 8/2008 | Palermo et al. |
| 2009/0036962 A1 | 2/2009 | Zierhofer |
| 2009/0157149 A1 | 6/2009 | Wahlgren et al. |
| 2010/0191311 A1 | 7/2010 | Scheiner et al. |

* cited by examiner $$\frac{\partial u}{\partial t} = \frac{\partial^2 u}{\partial x^2} - i(u,v) + P(x,t) + \sum_{i=1}^{n} S_i(x_i,t)$$

$$i(u,v) = \begin{cases} \lambda u & \text{for } u < v \\ (u-1) & \text{for } u \geq v \end{cases} \quad (1)$$

$$\frac{\partial v}{\partial t} = \varepsilon(\zeta u + v_r - v)$$

$$v_r = \alpha - \beta T_0, \alpha > 0, \beta > 0 \quad (2)$$

(A)

(B)

(A)

(B)

(C)

US 9,144,682 B2

METHOD AND SYSTEM OF STIMULATION OF NERVE TISSUE WITH A SEQUENCE OF SPATIALLY DISTRIBUTED RESONANT SUB-THRESHOLD ELECTRICAL STIMULI

RELATED APPLICATIONS

This application is a continuation of U.S. patent application Ser. No. 13/988,728, filed Aug. 23, 2013, now allowed, which is a 35 U.S.C. §371 national phase entry of PCT Application PCT/US2011/062807, filed Dec. 1, 2011, and published in English on Jun. 28, 2012, as International Publication No. WO 2012/087530, and which claims the benefit of U.S. Provisional Patent Application Ser. No. 61/424,758, filed Dec. 20, 2010, the disclosure of each of which is incorporated herein by reference in its entirety.

FIELD OF THE INVENTION

The present invention relates to functional electrical stimulation of nerve tissue. The invention's method is based on a concept of non-linear resonance and may be implemented for acceleration and stabilization of a wave propagating in nerve tissue with critically impaired excitation.

BACKGROUND OF INVENTION

Post-traumatic adjustment of pulse propagation in nerves with reduced excitability is a challenging biomedical and technological problem. In many cases such adjustments can be achieved with surgical interventions. However, surgery does not necessarily restore nerve conductivity to its pre-trauma levels, therefore still impaired conduction may cause partial or complete muscular paralysis. In this case propagation of excitation waves can be enforced only by applying external functional electrical stimulation (FES) using implantable [1] or surface stimulation electrodes [2-4]. This method has been confirmed as an effective tool for restoration of movement of paralyzed muscles in individuals with variety of neurological impairments [5].

Computerized systems for control of FES can deliver sequences of electrical stimuli with different frequency, amplitude and duration [6]. Commonly, these systems include variety of control units and electrical leads with multiple array or patch type stimulation electrodes. These electrodes deliver programmable stimuli, which are designed to maximize the effect of stimulation based on configuration of a particular stimulation field [7-10].

Successful FES process of functional restoration of muscle contraction depends on ability of nerve tissue to adequately conduct action potential. It also depends on excitation-contraction coupling in neuromuscular junctions, which transmit nervous impulses to muscular fibers. If any of these steps is impaired muscle does not contract normally. Usually, after severe neuromuscular injuries nerve conductivity is significantly reduced which, in turn, prevents the passage of excitation waves through neuromuscular transmitters. Under these circumstances propagation of excitation pulses is marginally stable and implementation of FES necessitates a significant increase of frequencies and amplitudes of functional electrical stimuli. The latest, instead of stabilization of propagation, can facilitate conduction blocks and may completely disrupt the process of training paralyzed muscles.

Accordingly, there is a need for new methods, systems and apparatus for stimulating excitable tissues which treat the problem of conduction instability and blockage therein.

SUMMARY OF THE INVENTION

A first aspect of the invention is a method of stimulating an excitable tissue (e.g., in vitro, in vivo) with a primary electrical stimulus through a primary electrode at a primary stimulation frequency, to produce a propagating action potential in the excitable tissue. The invention comprises concurrently stimulating the excitable tissue with a secondary electrical stimulus through at least one secondary electrode at a secondary stimulation frequency. The primary and secondary stimulation frequencies are preferably different from one another. The secondary electrical stimulus preferably has an amplitude not more than one third that of the primary electrical stimulus. Preferably, propagation of the action potential in the excitable tissue is enhanced (e.g., when propagation of action potentials in the tissue is otherwise unstable, partially blocked, or fully blocked).

In some embodiments, the primary stimulation frequency is from 1 or 5 Hertz up to 12 or 20 Hertz (most preferably about 8 hertz).

In some embodiments, the secondary stimulation frequency is from 1 to 15 percent greater than, or 1 to 15 percent less than, the primary stimulation frequency.

In some embodiments, the secondary electrical stimulus has an amplitude not more than one tenth that of the primary electrical stimulus.

In some embodiments, the at least one secondary electrode comprises a plurality of secondary electrodes (e.g., 3, 4, or 5 or more secondary electrodes), the plurality forming an array. In some embodiments, the array comprises: a leading electrode positioned on the tissue adjacent the primary electrode; a trailing electrode positioned on the tissue remote from the primary electrode (e.g., about 1 to 4 centimeters from the primary electrode; and optionally, one or more (e.g., from 1 to 5) intervening electrodes positioned on the tissue between the leading electrode and the trailing electrode.

In some embodiments, the primary electrical stimulus has a duration of from 0.1 or 0.2 seconds to 1 or 2 seconds (preferably about one half second).

In some embodiments, the secondary electrical stimulus has a duration of from 0.1 or 0.2 seconds to 1 or 2 seconds (preferably about one half second).

In some embodiments, the excitable tissue is peripheral nerve tissue (e.g., a motor nerve; a sensory nerve).

In some embodiments, the excitable tissue is injured.

A further aspect of the invention is a tissue stimulator for use in carrying out a method as described herein, and/or configured to carry out a method as described herein. Such a tissue stimulator may generally comprise a power supply, a primary electrode, at least one secondary electrode, and a controller configured for carrying out a method as described herein. In some embodiments, the at least one secondary electrode comprises a plurality of secondary electrodes.

A further aspect of the invention is the use of a first stimulus and a second stimulus as described herein for carrying out a method as described herein.

The present invention is readily distinguished from prior art such as U.S. Pat. No. 7,689,289 to King et al. and U.S. Pat. No. 6,473,653 to Schallhorn et al. King et al. reconfigures an excitation pattern by applying two spatially distinguished sub-threshold electrical stimuli. These stimuli create a superposition of local electric fields and induce additional supra-threshold excitation zones. In Schallhorn et al., reconfiguration of excitation pattern is achieved by a controlled activation of multiple spatially distributed stimulation sites combined in one lead. Both are simply dealing with reconfiguring of stationary excitation patterns using multiple spatially distributed periodic stimuli. Neither address dynamic features of the nerve action potential and in no way relate to stabilization of its propagation.

The present invention is explained in greater detail in the drawings herein and the specification set forth below.

DETAILED DESCRIPTION OF ILLUSTRATIVE EMBODIMENTS

Figure 1A:
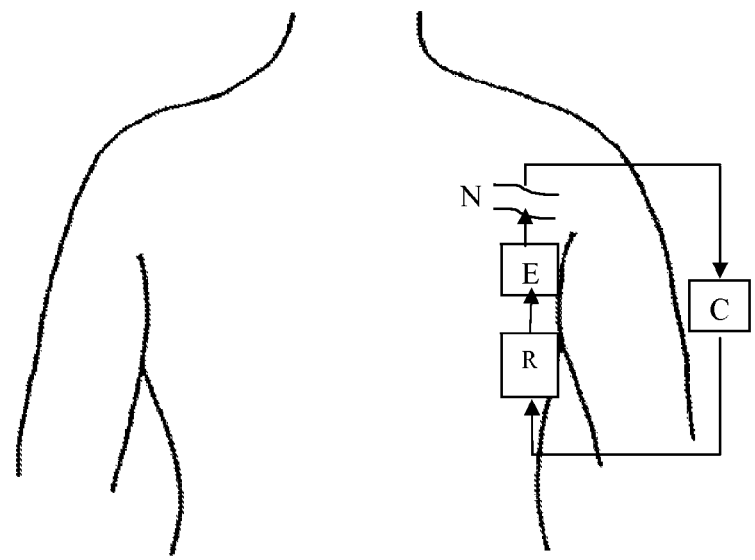
FIG. 1A is a schematic limb placement of the external (percutaneous) control unit (C) wirelessly connected with an implantable receiver (R) which simultaneously activates multiple spatially distributed stimulation sites in the implantable electrode (E)

The present invention now will be described more fully hereinafter with reference to the accompanying figures, in which embodiments of the invention are shown. This invention may, however, be embodied in many alternate forms and should not be construed as limited to the embodiments set forth herein. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

The present invention may be embodied as systems, methods, and/or computer program products. Accordingly, the present invention may be embodied in hardware and/or in software (including firmware, resident software, micro-code, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, electromagnetic, infrared, or semiconductor system, apparatus, or device. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), and a portable compact disc read-only memory (CD-ROM).

The present invention may be described below with reference to block diagrams and/or flowchart illustrations of devices, methods and computer program products according to embodiments of the invention. It is to be understood that the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

Applicants specifically intend that the disclosures of all United States patent references cited herein be incorporated by reference herein in their entirety.

"Action potential" is a consecutive rise and fall of the individual cellular transmembrane potential difference which results from cyclic changes in concentration of ions between extra- and intra-cellular spaces.

"Propagation" of action potential is a diffusive transfer of action potentials from one cellular membrane to another which occurs due to changes of concentration of extra-cellular ions between the neighboring cellular membranes.

"Excitable tissue" as used herein includes muscle tissue (e.g., skeletal muscle, smooth muscle) and nerve tissue (e.g., peripheral motor nerves; peripheral sensory nerves). The tissue is typically mammalian and in a preferred embodiment is human. The tissue may be in vitro, or in vivo in a subject.

"Subject" as used herein is, in general, male or female human subjects of any suitable age, including juvenile, adolescent, adult, and geriatric subjects.

"Injured" as used herein with respect to an excitable tissue refers to a tissue that has sustained a chemical injury (chemical burn, toxicological injury), mechanical injury (crushed, lacerated, fully or partially severed) or the like, such that propagation of a conducted signal therein is impaired.

"Electrical stimulus" as used herein typically refers to a waveform electrical stimulus: That is, an electrical stimulus having a repeating series of peaks of generally uniform spacing or time interval therebetween, which time interval can be expressed as a frequency in Hertz. Any suitable waveform shape can be used, including but not limited to square, ramped, sawtooth, sine, logarithmic, exponential, and combinations thereof. The waveform shapes can be modulated, truncated, cut, rectified, etc., as is known in the art. Primary and secondary electrical stimuli as described herein can have the same, or different, waveform shapes.

"Concurrently" as used herein with respect to primary and secondary electrical stimuli means at the same time, or at least partially overlapping in time.

The present invention overcomes limitations of the conventional FES method and implements a novel technique of applying distributed sequence of secondary sub-threshold stimuli resonant with a frequency of primary stimulations. The present invention is based on the discovery that such non-linear resonant frequency locking stabilizes propagation at higher primary stimulation frequencies, thus, facilitating conditions for more effective restoration of paralyzed muscles, and/or the treatment of pain such as neuropathic pain arising from injured sensory nerves. This method can be especially instrumental in tissues with severely impaired conductivity where propagation of a primary wave alone without resonant secondary stimuli would be completely blocked.

In one non-limiting illustrative embodiment, the present invention provides a method of stimulating excitable tissue by resonant spatially distributed stimuli to provide greater stability of propagation of a primary excitation wave. The method comprises the steps of:

(a) determining if the primary rhythm contains a propagation block at a particular primary stimulation frequency;
(b) if yes, applying additional sub-threshold stimuli at a secondary stimulation frequency after the first primary wavefornt passes the last electrode in the chain of secondary stimulation sites;
(c) continuing sufficient number of primary and secondary stimulation sequencies and rechecking for propagation block;
(d) adjusting the number and frequency of secondary stimuli if a propagation block is still present;
(e) repeating steps (b)-(d) until a resonant frequency locking is achieved and each primary wave results from a single corresponding primary stimulation without intermediate propagation blocks.

An illustrative system for implementing is depicted in FIG. 1. In general, the system comprises:

(a) implantable device with a primary electrode and a grid of secondary electrodes which together form a one-dimensional array of stimulation sites;
(b) percutaneous receiver/stimulator
(c) external controller/transmitter The system has four major functions. The first one is using primary electrode to deliver over-threshold stimuli to initiate a chain of primary excitation waves. The second one is using an electrode array and receiver/stimulator to detect conduction blocks that prevent the primary excitation wave to propagate between any pair of successive stimulation sites. The third function is using controller/transmitter to transmit a corresponding signal and adjust stimulation parameters accordingly if a conduction block has been detected. The fourth function is using receiver/stimulator to deliver secondary sub-threshold stimulation pulses, which stabilize propagation of a marginally stable primary excitation wave.

The magnitude of stimulation parameters and a number of stimulation sites activated during such a feedback process can be adjusted either automatically or using manual programming of an external controller.

In some embodiments, the present invention accordingly provides a technique for restoration and training paralyzed muscles in patient when propagation of neural impulses is marginally stable or completely blocked.

In some embodiments, the present invention provides a technique for restoration and training paralyzed muscles in patient at higher functional stimulation frequencies.

In still other embodiments, the present invention provides a technique for restoration and training paralyzed muscles in patients with severe damage of neurological tissues.

Those skilled in the art will appreciate numerous additional embodiments of the present invention, based on known systems and methods and variations thereof that will be readily apparent to those skilled in the art. See, e.g., U.S. Pat. Nos. 3,662,758; 3,727,616; 4,524,774; 6,473,653; and 7,689,289; see also P. Peckahm and J. Knutson, *Anna Rev. Biomed. Eng.* 7: 327-60 (2005). Accordingly, the foregoing is set forth for illustrative purposes only, and is not to be construed as limiting thereof.

The controller (typically implemented as circuitry and/or software) can be provided in a housing, such as sealed housing suitable for implantation if desired, or a housing for carrying on or association with a patient (similar to a TENS unit). The power supply (e.g., a battery) can be contained within the housing or located separately therefrom. While the controller is described in combination with the electrodes above, it will be appreciated that the controller may also be provided as a subcombination, with connectors (e.g., mounted on the housing and in turn connected to the controller circuitry) provided for connecting removable or disposable electrodes thereto.

The present invention is explained in greater detail in the following non-limiting Examples.

EXAMPLE 1

Simulation of Propagation of Excitation Waves in One-Dimensional Nerve Tissue

Figure 1B:
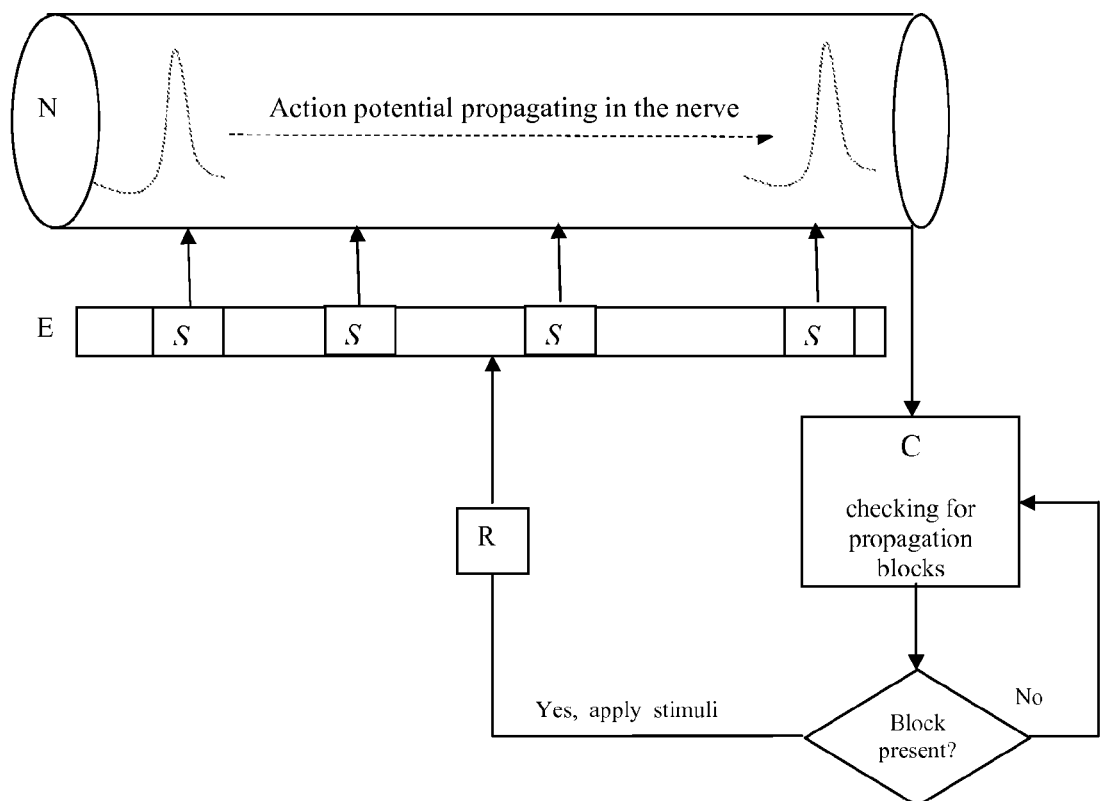
FIG. 1B is a block diagram of stabilization of marginally stable action potential propagation in the nerve using a set of additional spatially distributed sub-threshold stimuli (S).
Figure 2:
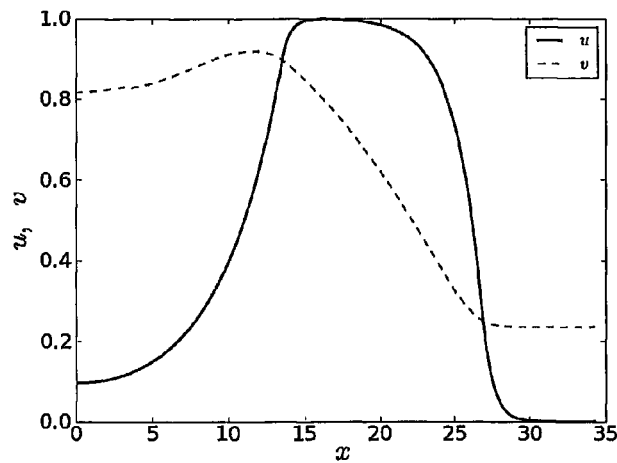
FIG. 2 depicts the equations used in a simplified mathematical model of propagation of non-linear resonant excitation waves. It also depicts a typical propagating action potential.

This example was carried out to simulate a practical realization of the system shown in FIG. 1A. FIG. 1B visualizes propagation of excitation waves which results from a superposition of main (primary) pulse and spatially distributed secondary stimulations applied to one-dimensional excitable cable. For our simulations we implemented rate dependent modification of analytically solvable two variable Chernyak-Starobin-Cohen (CSC) reaction diffusion model [11-13] as depicted in FIG. 2A. Equations (1),(2) describe the process of propagation of excitation in an one-dimensional excitable cable of finite length with linear dependence of excitation threshold (memory) on period of primary stimulations [14].

In this model, functions $u(x, t)$ and $v(x, t)$ are the membrane potential and slow recovery current, respectively. Parameter $v_r$ is the critical excitation threshold necessary to initiate the propagation of an action potential through the cable. Another parameter of the model, $\epsilon$, reflects the two order-of-magnitude difference in time constants between the fast excitation and slow recovery processes.

According to the method of the present invention, a set of primary and secondary excitation sources formed a spatially distributed array of independent stimulation sites. The first site near the cable left end was a primary stimulation site. Over-threshold stimuli $P(x, t)$ applied at this site initiated a sequence of primary excitation waves which propagated through the cable from left to right with a period $T_0$ and amplitude $A_0$. Secondary sub-threshold stimuli $S_i(x_i,t)$ were applied at other stimulation sites with a period T and amplitude A, respectively. Secondary stimuli did not initiated additional waves, but provided additional charge to accelerate the propagation of primary waves.

If the first primary stimulus applied to a cable at rest ($v(x, t=0)=v_r$) has a sufficient amplitude to overcome the excitation threshold $v_r$, it will initiate action potential which will propagate along the cable. During the depolarization phase the magnitude of action potential, u, rises from its equilibrium state ($u(x, t=0)=0$) to the value of unity, while v rises from its resting value of $v_r$. The intersection between the values of u and v defines the begining of the action potential. During the repolarization phase (refractory period) both u and v decrease from their maximum values toward corresponding resting values. This results in a second intersection between u and v near which marks the end of the action potential duration (FIG. 2B). At any particular spatial point of interest the action potential duration, $T_{AP}$, was computed as the time interval between successive intersections of u and v. Action potential computations were performed after delivering 80 primary stimuli to ensure that all corresponding measurements reflected steady state values of $T_{AP}$.

Figure 3:
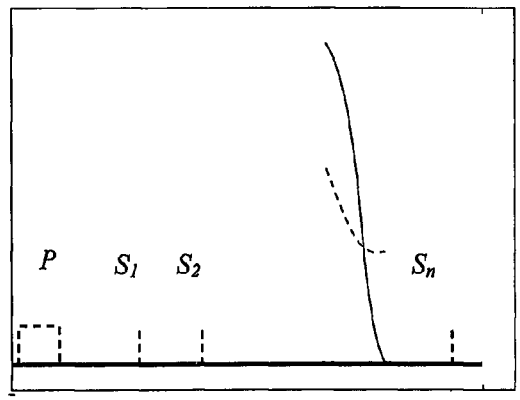
FIG. 3 Spatial configuration of primary and secondary stimulation sites.

In general, there may be n secondary sources of stimulation, $S_i(x_i,t)$, which can be located at any point of the cable (FIG. 3). In our simulations we used six equidistant secondary sites located between $x=40\Delta x$ and $x=140\Delta x$. The primary stimuli P(x,t) (red dotted line) were applied at every point between $x=2\Delta x$ and $x=15\Delta x$. Here $\Delta x=0.23$ is a spatial grid interval. The number of spatial nodes was equal to 150. For all simulations model parameters were equal to $\epsilon=0.1, \zeta=1.1, \lambda=0.4, A_0=1.4$.

Rate dependent excitation threshold $v_r=\alpha-\beta T_0$ was determined by two constants 0.31 and 0.0025 for $\alpha$ and $\beta$, respectively. Secondary stimulations were simultaneously initiated at all six secondary sites after the first primary wavefront (intersection between u and v) reached the end of the cable. A phase shift between the onset of primary and secondary stimuli was determined by the value of primary stimulation period.

EXAMPLE 2

Figure 4:
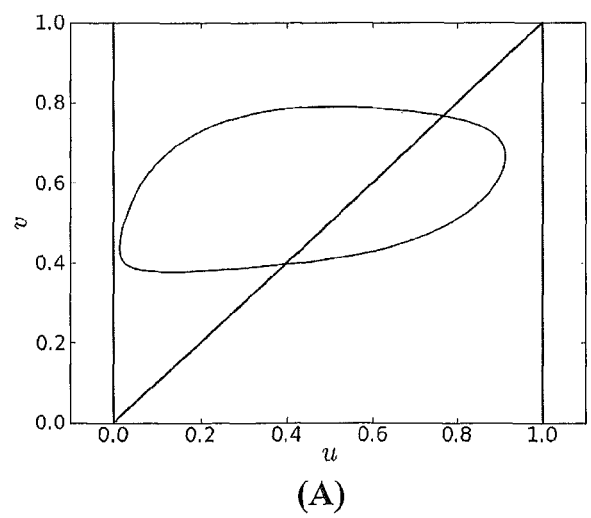
FIG. 4 Phase portrait of the system with and without additional excitation from the secondary sources of stimulation.
Figure 4:
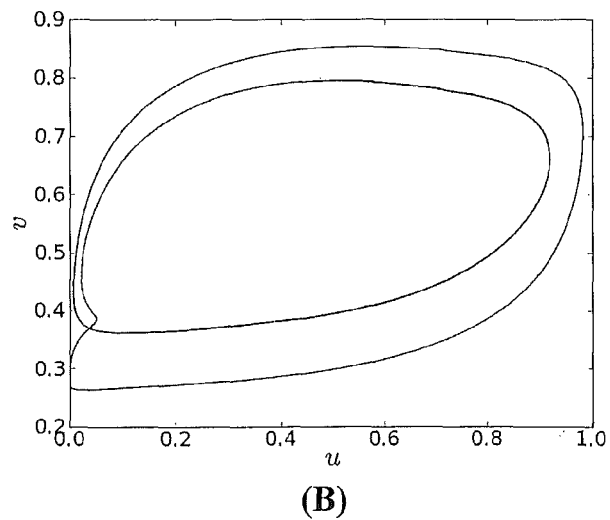
Figure 4:
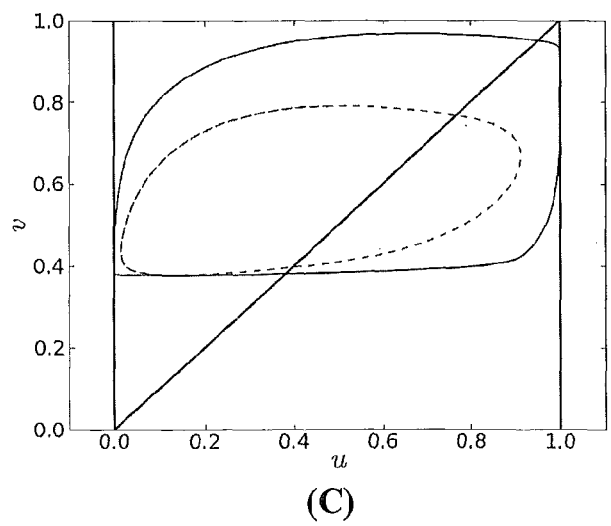

Phase Portraits at Marginal Stability of Propagation with and without Additional Stimuli This example was carried out to ascertain a principle of stabilization of excitation wave using additional sub-threshold stimulations. At sufficiently long periods of stimulation a slow recovery current v has enough time to reach its equilibrium state $v_r$ before the next stimulus is applied to the cable. However, at shorter periods v does not completely recover and its minimum value, $v_{min}$, is still greater than the excitation threshold $v_r$ (FIG. 4A). Below a certain value of primary stimulation period $T_{end}$ recovery current v becomes so much higher than $v_r$, that the next primary stimulus may not result in initiation of a complete action potential. The latest may lead to instabilities that can occur in the form of alternating action potentials (alternans) or complex M:N (M>N) conduction blocks (FIG. 4B).

The present invention demonstrates that such instabilities can be preempted by applying additional sub-threshold spatially distributed stimuli. FIG. 4C (dashed line) shows a phase portrait of the solution of Eqs. (1)-(2) in the absence of secondary excitations for $T_{end}=30$ and $v_r=0.24$. In this case propagation of excitation wave is at a margin of stability and therefore a countour of u significantly deviates from its N-shaped nullcline shown in black. Further decrease in primary stimulation period below the critical value $T_0^* < T_{end}$ results hi conduction blocks as depicted in FIG. 4B. On the contrary, FIG. 4C (solid line) demonstrates that propagation can be stabilized, if the secondary stimuli with sub-threshold amplitudes $A=0.1A_0$ and periods $T=T_0^*$ are applied in addition to primary stimulations.

EXAMPLE 3

Figure 5:
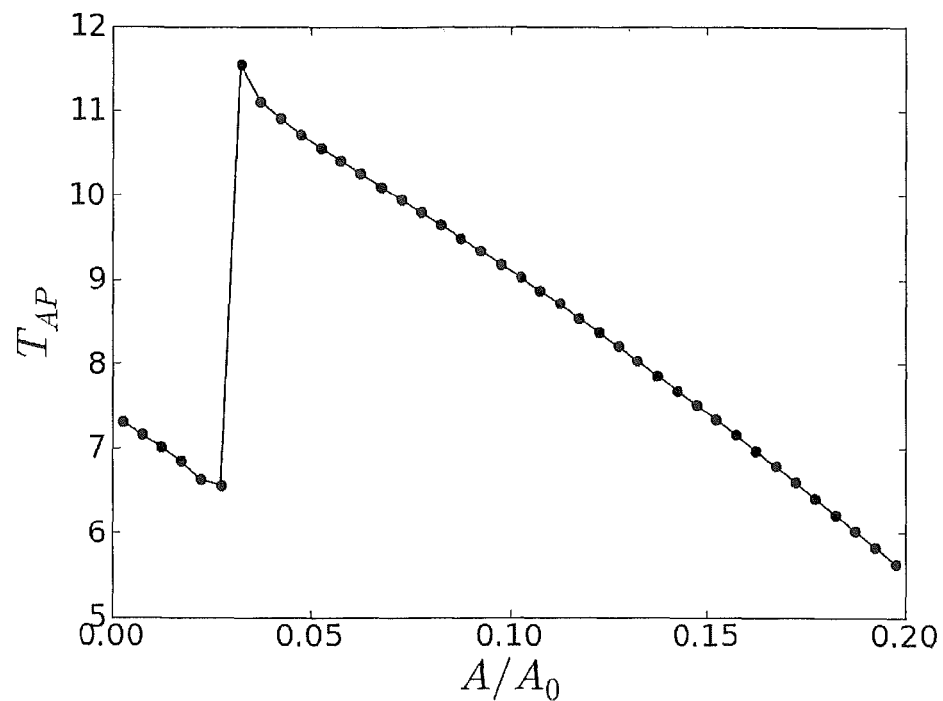
FIG. 5 Dependence of action potential duration $T_{AP}$ for different amplitudes of secondary stimuli.

Dependence of Safely Margin of Stability of Propagation on Amplitude of Secondary Stimuli This example was carried out to demonstrate a resonant nature of dependence of action potential duration, $T_{AP}$, on amplitude of secondary stimuli. Period of primary and secondary stimulations were the same ($T_0=30$, $v_r=0.24$) while the amplitude A varied from 0 to $0.2A_0$. Action potential duration was measured away from the site of a primary source at the mid point of the cable $x=L/2$. Dependence of action potential duration on A revealed a typical resonant behavior, thereby $T_{AP}$ decreased for amplitudes smaller and greater than resonant value of $0.0025A_0$ (FIG. 5).

EXAMPLE 4

Figure 6:
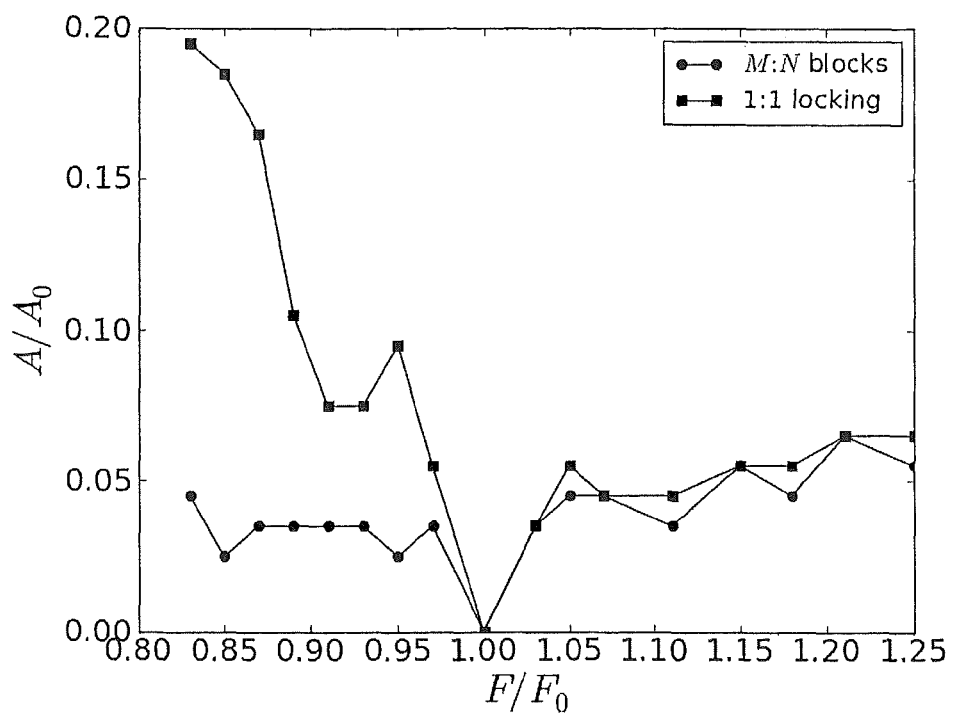
FIG. 6 Action potential resonant locking mechanism at different frequencies and amplitudes of the secondary stimuli.

Resonant Action Potential Locking for Different Amplitudes and Frequencies of Secondary Stimuli This example was carried out to demonstrate the dependence of resonant action potential locking on amplitude and frequency of secondary stimulations at a constant frequency of primary stimuli $$F_0 = \frac{1}{T_0}, T_0 = 30. \quad \text{(FIG. 6)}$$

It has been observed that locking of action potential (1:1 response) at each given secondary stimulation frequency F occured for A which were greater than certain critical values shown by a curve marked with squares. At lower values of A, action potentials exhibited more complex responses encircled by a curve marked with circles (M:N, M>1). Below this curve there was no locking and the cable responded only to primary stimulations. An amplitude-frequency locking boundary was assymetrical with respect to frequency of primary stimulations, thereby the amplitude margin at $F<F_0$ was higher than at $F>F_0$.

EXAMPLE 5

Dependence of the Minimal Period $T_{end}$ of Primary Stable Waves on Frequency Ratio $$\frac{F}{F_0}$$

for Different Values of A

Figure 7:
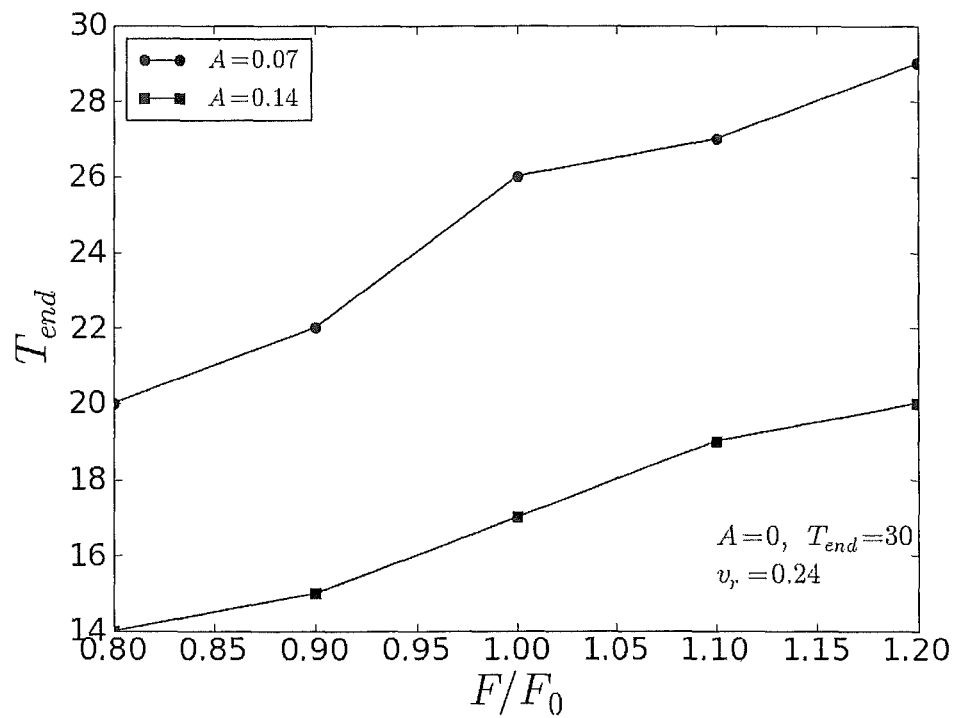
FIG. 7 Dependence of a minimal stable action potential duration on frequency ratio for different amplitudes of secondary stimuli.

This example was carried out to demonstrate the increase of safety margin of stability of primary waves at higher amplitudes of secondary stimuli. FIG. 7 shows that for higher amplitudes of secondary stimuli regardless the value of secondary-primary frequency ratio stable 1:1 primary responses occur at significantly lower values of $T_{end}$. The increase of safety margin of stability is more substantial as the amplitudes of secondary stimuli increase from A=0.07 (curve with circles) to A=0.14 (curve with squares), and the minimal value of $T_{end}$ decreases by more than 30% regardless of frequency ratio. For both curves the values of $T_{end}$ are significantly smaller than that equal to 30 in the absence of secondary stimuli.

EXAMPLE 6

Figure 8:
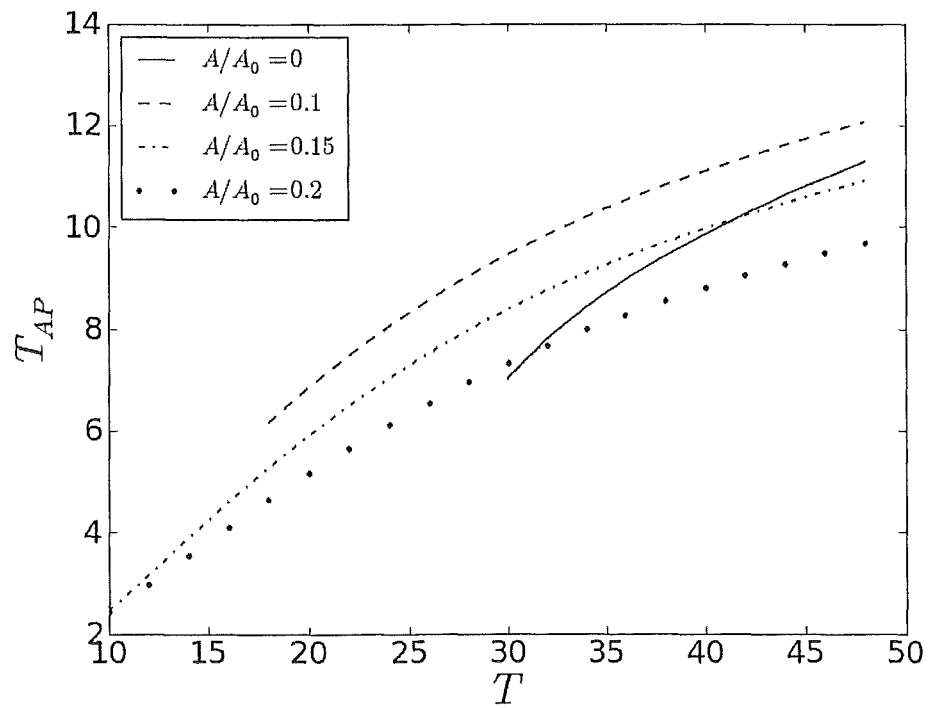
FIG. 8 Dependence of action potential duration of a primary excitation on period on period of primary stimulations for different values of amplitudes of secondary stimuli.

Steady State Restitution Dependences $T_{AP}$ on Period of Secondary Stimulations T for Different Values of Amplitudes of Secondary Stimuli This example was carried out to extend results from the example 5 and demonstrate stabilization of propagation of primary waves in a wide range of stimulation periods T (FIG. 8). In this example values of periods of secondary stimulations T were equal to a primary stimulation period $T_0$. FIG. 8 shows that propagation of primary waves is more stable in the presence of secondary stimulations for different values of T. Indeed, safety margin of stability of propagation significantly increases for higher amplitudes and allows more stable propagation for lower $T_{AP}$ and lower minimal values of $T_{end}$.

EXAMPLE 7

Dependence of $T_{end}$ on Different Number of Secondary Sources

Figure 9:
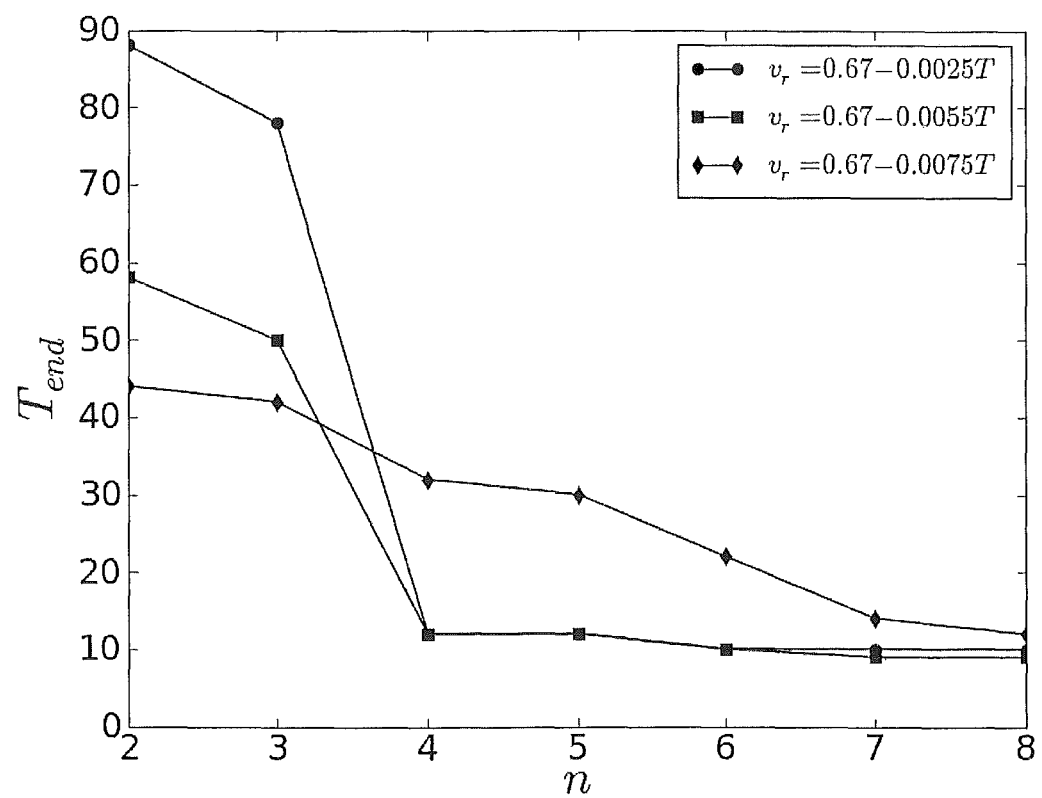
FIG. 9 Dependence of a minimal stable action potential duration on a number of secondary sources of stimulation.

This example was carried out to determine the optimal number of secondary stimulation sources. The dependence of $T_{end}$ on number of secondary sources was determined for n ranging from 2 to 8 for three sets of rate dependence parameters $\alpha$ and $\beta$ (FIG. 9). The amplitude of secondary stimuli was constant and equal to $0.1 A_0$. The value $T_{end}$ decreased for higher n and saturated beyond a certain number at each set of parameters $\alpha$ and $\beta$.

REFERENCES

1. C. Veraat, W. M. Grill, T. Mortimer. Selective control of muscle activation with a multipolar nerve cuff electrode. *IEEE Transactions on Biomedical Engineering* 40 (1993): 640-653
2. R. A. Thorsen, E. Occhi, S. Boccardi et. al. Functional electrical stimulation reinforced tenodesis effect controlled. *Journal of Rehabilitation Research & Development* 43 (2006): 247-256
3. K. Ambrose, M. A. Wilmarth Functional electrical stimulation for treatment of chronic foot drop due to an incomplete sacral nerve root lesion: A case study. *The Foot and Ankle Online Journal* 3, no. 8 (2010)
4. E. C. Tuday, K. S. Olree, K. W. Horch Differential activation of nerve fibers with magnetic stimulation in humans. *BMC Neuroscience* 7 (2006): 58-64
5. P. H. Peckham, J. S. Knutson Functional electrical stimulation for neuromuscular applications *Anna Rev. Biomed. Eng* 7 (2005): 327-360
6. S. Trier, T. Vrabec, J. Weisgarber Using functional electrical stimulation to restore movement to individuals with neuromuscular disabilities. Matlab Digest, Academic Edition (2010) www.mathworks.com
7. S. M. Goetz, R. T. Stone, W. W. Ball et. al. Stimulation templates for programming a stimulation lead with complex electrode array geometry. U.S. Pat. No. 7,676,273 (2010)
8. S. M. Goetz, R. T. Stone, W. W. Ball et. al. Programming interface with an unwrapped 2D view of a stimulation lead with complex electrode array geometry. U.S. Pat. No. 7,657,319 (2010)
9. M. T. Gerber Electrical stimulation lead with conformable array of electrodes. U.S. Pat. No. 7,769,472 (2010)
10. A. Dar and R. H. Nathan Scanning electrode system for a neuroprosthesis. U.S. Pat. No. 7,149,582 (2006)
11. Y. B. Chernyak, J. M. Starobin, R. Cohen Class of exactly solvable models of excitable media. *Physical Review Letters* 80 (1998): 5675-5678.
12. Y. B. Chernyak, J. M. Starobin, R. J. Cohen, Where do dispersion curves end? A basic question in theory of excitable media. *Phys. Rev. E* 58 (1998): 4108-4111
13. I. B. Schwartz, I. Triandaf, J. M. Starobin et al. Origin of quasiperiodic dynamics in excitable media, *Phys. Rev. E*, 61 (2000): 7208-7211
14. J. M. Starobin, C. P. Danford, V. Varadarajan et al. Critical scale of propagation influences dynamics of waves in a model of excitable medium, *Nonlinear Biomedical Physics* 2009, 3:4

The foregoing is illustrative of the present invention, and is not to be construed as limiting thereof. The invention is defined by the following claims, with equivalents of the claims to be included therein.

We claim:

1. In a method of stimulating an excitable tissue with a primary electrical stimulus through a primary electrode at a primary stimulation frequency, to produce a propagating action potential in said excitable tissue, the improvement comprising:
   concurrently stimulating said excitable tissue with a secondary electrical stimulus through at least one secondary electrode at a secondary stimulation frequency;
   wherein said primary and secondary stimulation frequencies are different from one another;
   and wherein said secondary electrical stimulus has an amplitude not more than one third that of said primary electrical stimulus;
   so that propagation of said action potential in said excitable tissue is enhanced.

2. The method of claim 1, wherein said primary stimulation frequency is from 1 Hertz up to 20 Hertz.

3. The method of claim 1, wherein said secondary stimulation frequency is from 1 to 15 percent greater than, or 1 to 15 percent less than, said primary stimulation frequency.

4. The method of claim 1, wherein secondary electrical stimulus has an amplitude not more than one tenth that of said primary electrical stimulus.

5. The method of claims 1, wherein said at least one secondary electrode comprises a plurality of secondary electrodes, said plurality forming an array.

6. The method of claim 1, wherein said array comprises:
   a leading electrode positioned on said tissue adjacent said primary electrode;
   a trailing electrode positioned on said tissue remote from said primary electrode; and
   optionally, one or more intervening electrodes positioned on said tissue between said leading electrode and said trailing electrode.

7. The method of claim 1, wherein said primary electrical stimulus has a duration of from 0.1 seconds to 2 seconds.

8. The method of claim 1, wherein said secondary electrical stimulus has a duration of from 0.1 second to 2 seconds.

9. The method of claim 1, wherein said excitable tissue is peripheral nerve tissue.

10. The method of claim 1, wherein said excitable tissue is injured.

11. A tissue stimulator comprising:
(a) a primary electrode array for stimulating an excitable tissue;
(b) at least one secondary electrode for concurrently stimulating said excitable tissue; and
(c) a controller operatively associated with said primary electrode array and said at least one secondary electrode, with
   (i) said controller configured to stimulate said excitable tissue through said primary electrode array with a primary electrical stimulus at a primary stimulation frequency, to produce a propagating action potential in said excitable tissue; and with
   (ii) said controller configured to concurrently stimulate said excitable tissue through said at least one secondary electrode with a secondary electrical stimulus at a secondary stimulation frequency;
said controller further configured so that said primary and secondary stimulation frequencies are different from one another; and wherein said secondary electrical stimulus has an amplitude not more than one third that of said primary electrical stimulus; so that propagation of said action potential in said excitable tissue is enhanced.

12. The tissue stimulator of claim 11, wherein said primary stimulation frequency is from 1 Hertz up to 12 Hertz.

13. The tissue stimulator of claim 11, wherein said secondary stimulation frequency is from 1 to 15 percent greater than, or 1 to 15 percent less than, said primary stimulation frequency.

14. The tissue stimulator of claim 11, wherein secondary electrical stimulus has an amplitude not more than one tenth that of said primary electrical stimulus.

15. The tissue stimulator of claim 11, wherein said at least one secondary electrode comprises a plurality of secondary electrodes.

16. The tissue stimulator of claim 11, wherein said array comprises:
a leading electrode positioned on said tissue adjacent said primary electrode;
a trailing electrode positioned on said tissue remote from said primary; and
optionally, one or more intervening electrodes positioned on said tissue between said leading electrode and said trailing electrode.

17. The tissue stimulator of claim 11, wherein said primary electrical stimulus has a duration of from 0.1 seconds to 2 seconds.

18. The tissue stimulator of claim 11, wherein said secondary electrical stimulus has a duration of from 0.1 seconds to 2 seconds.

19. The tissue stimulator of claim 11, wherein said excitable tissue is peripheral nerve tissue.

20. The tissue stimulator of claim 11, wherein said excitable tissue is injured.

21. The tissue stimulator of claim 11, further comprising a power supply operatively associated with said controller.

22. The tissue stimulator of claim 11, wherein said at least one secondary electrode comprises a plurality of secondary electrodes.

* * * * *